(12) United States Patent
Ziobro

(10) Patent No.: US 8,556,932 B2
(45) Date of Patent: Oct. 15, 2013

(54) COLLAPSIBLE PLUG FOR TISSUE CLOSURE

(75) Inventor: John M. Ziobro, Sunnyvale, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/111,371

(22) Filed: May 19, 2011

(65) Prior Publication Data
US 2012/0296372 A1   Nov. 22, 2012

(51) Int. Cl.
*A61B 17/04* (2006.01)

(52) U.S. Cl.
USPC .......................................................... 606/213

(58) Field of Classification Search
USPC ................................. 606/213–215
See application file for complete search history.

(56) References Cited

U.S. PATENT DOCUMENTS

| | | |
|---|---|---|
| 287,046 A | 10/1883 | Norton |
| 1,088,393 A | 2/1914 | Backus |
| 1,331,401 A | 2/1920 | Summers |
| 2,087,074 A | 7/1937 | Tucker |
| 2,453,227 A | 11/1948 | James |
| 2,684,070 A | 7/1954 | Kelsey |
| 2,944,311 A | 7/1960 | Schneckenberger |
| 2,969,887 A | 1/1961 | Darmstadt et al. |
| 3,015,403 A | 1/1962 | Fuller |
| 3,142,878 A | 8/1964 | Santora |
| 3,482,428 A | 12/1969 | Kapitanov et al. |
| 3,586,002 A | 6/1971 | Wood et al. |
| 3,604,425 A | 9/1971 | Le Roy |
| 3,677,243 A | 7/1972 | Nerz |
| 3,757,629 A | 9/1973 | Schneider |
| 3,805,337 A | 4/1974 | Branstetter |
| 3,874,388 A | 4/1975 | King et al. |
| 3,944,114 A | 3/1976 | Coppens |
| 4,014,492 A | 3/1977 | Rothfuss |
| 4,192,315 A | 3/1980 | Hilzinger et al. |
| 4,207,870 A | 6/1980 | Eldridge |
| 4,217,902 A | 8/1980 | March |
| 4,278,091 A | 7/1981 | Borzone |
| 4,317,445 A | 3/1982 | Robinson |
| 4,318,401 A | 3/1982 | Zimmerman |

(Continued)

FOREIGN PATENT DOCUMENTS

| | | |
|---|---|---|
| DE | 197 11 288 | 10/1998 |
| DE | 29723736 U1 | 4/1999 |

(Continued)

OTHER PUBLICATIONS

U.S. Appl. No. 11/675,462, mailed Dec. 22, 2011, Notice of Allowance.

(Continued)

*Primary Examiner* — Darwin Erezo
(74) *Attorney, Agent, or Firm* — Workman Nydegger; Randy Shen

(57) ABSTRACT

A tissue closure device includes a collapsible plug and an actuator. The plug has a surface extending between a proximal face and an opposing distal face. A lumen extends through the plug between the proximal and distal faces along a longitudinal axis. The plug is collapsible between a non-collapsed state in which the lumen is open and a collapsed state in which the lumen is closed. The actuator is configured to move the plug between the non-collapsed state and the collapsed state by being pulled proximally, such as through the lumen.

19 Claims, 5 Drawing Sheets

(56) References Cited

U.S. PATENT DOCUMENTS

| | | | |
|---|---|---|---|
| 4,345,606 A | 8/1982 | Littleford | |
| 4,396,139 A | 8/1983 | Hall et al. | |
| 4,407,286 A | 10/1983 | Noiles et al. | |
| 4,411,654 A | 10/1983 | Boarini et al. | |
| 4,412,832 A | 11/1983 | Kling et al. | |
| 4,428,376 A | 1/1984 | Mericle | |
| 4,485,816 A | 12/1984 | Krumme | |
| RE31,855 E | 3/1985 | Osborne | |
| 4,505,273 A | 3/1985 | Braun et al. | |
| 4,505,274 A | 3/1985 | Speelman | |
| 4,523,695 A | 6/1985 | Braun et al. | |
| 4,525,157 A | 6/1985 | Vailaincourt | |
| 4,586,503 A | 5/1986 | Kirsch et al. | |
| 4,607,638 A | 8/1986 | Crainich | |
| 4,610,251 A | 9/1986 | Kumar | |
| 4,610,252 A | 9/1986 | Catalano | |
| 4,665,906 A | 5/1987 | Jervis | |
| 4,687,469 A | 8/1987 | Osypka | |
| 4,724,840 A | 2/1988 | McVay et al. | |
| 4,738,658 A | 4/1988 | Magro et al. | |
| 4,744,364 A | 5/1988 | Kensey | |
| 4,771,782 A | 9/1988 | Millar | |
| 4,772,266 A | 9/1988 | Groshong | |
| 4,777,950 A | 10/1988 | Kees, Jr. | |
| 4,789,090 A | 12/1988 | Blake, III | |
| 4,832,688 A | 5/1989 | Sagae et al. | |
| 4,836,204 A | 6/1989 | Landymore et al. | |
| 4,852,568 A | 8/1989 | Kensey | |
| 4,860,746 A | 8/1989 | Yoon | |
| 4,865,026 A | 9/1989 | Barrett | |
| 4,874,122 A | 10/1989 | Froelich et al. | |
| 4,878,915 A | 11/1989 | Brantigan | |
| 4,886,067 A | 12/1989 | Palermo | |
| 4,887,601 A | 12/1989 | Richards | |
| 4,900,303 A * | 2/1990 | Lemelson | 604/514 |
| 4,917,087 A | 4/1990 | Walsh et al. | |
| 4,934,364 A | 6/1990 | Green | |
| 4,950,258 A | 8/1990 | Kawai et al. | |
| 5,007,921 A | 4/1991 | Brown | |
| 5,015,247 A | 5/1991 | Michelson | |
| 5,021,059 A | 6/1991 | Kensey et al. | |
| 5,026,390 A | 6/1991 | Brown | |
| 5,053,008 A | 10/1991 | Bajaj | |
| 5,061,274 A | 10/1991 | Kensey | |
| 5,100,418 A | 3/1992 | Yoon et al. | |
| 5,108,420 A | 4/1992 | Marks | |
| 5,108,421 A | 4/1992 | Fowler | |
| 5,114,032 A | 5/1992 | Laidlaw | |
| 5,114,065 A | 5/1992 | Storace | |
| 5,131,379 A | 7/1992 | Sewell, Jr. | |
| 5,147,381 A | 9/1992 | Heimerl et al. | |
| 5,156,609 A | 10/1992 | Nakao et al. | |
| 5,167,643 A | 12/1992 | Lynn | |
| 5,171,249 A | 12/1992 | Stefanchik et al. | |
| 5,176,648 A | 1/1993 | Holmes et al. | |
| 5,192,300 A | 3/1993 | Fowler | |
| 5,192,301 A * | 3/1993 | Kamiya et al. | 606/213 |
| 5,192,302 A * | 3/1993 | Kensey et al. | 606/213 |
| 5,209,756 A | 5/1993 | Seedhom et al. | |
| 5,222,974 A | 6/1993 | Kensey et al. | |
| 5,246,443 A | 9/1993 | Mai | |
| 5,275,616 A | 1/1994 | Fowler | |
| 5,290,243 A | 3/1994 | Chodorow et al. | |
| 5,290,310 A | 3/1994 | Makower et al. | |
| 5,292,309 A | 3/1994 | Van Tassel et al. | |
| 5,292,332 A * | 3/1994 | Lee | 606/213 |
| 5,304,184 A | 4/1994 | Hathaway et al. | |
| 5,306,254 A | 4/1994 | Nash et al. | |
| 5,318,542 A | 6/1994 | Hirsch et al. | |
| 5,320,639 A | 6/1994 | Rudnick | |
| 5,334,216 A | 8/1994 | Vidal et al. | |
| 5,334,217 A | 8/1994 | Das | |
| 5,350,399 A | 9/1994 | Erlebacher et al. | |
| 5,352,229 A | 10/1994 | Goble et al. | |
| 5,366,458 A | 11/1994 | Korthoff et al. | |
| 5,366,479 A | 11/1994 | McGarry et al. | |
| RE34,866 E | 2/1995 | Kensey et al. | |
| 5,395,030 A | 3/1995 | Kuramoto et al. | |
| 5,411,520 A | 5/1995 | Nash et al. | |
| 5,413,571 A | 5/1995 | Katsaros et al. | |
| 5,416,584 A | 5/1995 | Kay | |
| 5,417,699 A | 5/1995 | Klein et al. | |
| 5,419,765 A | 5/1995 | Weldon et al. | |
| 5,431,639 A | 7/1995 | Shaw | |
| 5,439,479 A | 8/1995 | Shichman et al. | |
| 5,443,481 A | 8/1995 | Lee | |
| 5,445,167 A | 8/1995 | Yoon et al. | |
| 5,451,235 A | 9/1995 | Lock et al. | |
| 5,456,400 A | 10/1995 | Shichman et al. | |
| 5,470,010 A | 11/1995 | Rothfuss et al. | |
| 5,474,557 A | 12/1995 | Mai | |
| 5,478,352 A | 12/1995 | Fowler | |
| 5,478,354 A | 12/1995 | Tovey et al. | |
| 5,486,195 A | 1/1996 | Myers et al. | |
| 5,507,755 A | 4/1996 | Gresl et al. | |
| 5,522,840 A | 6/1996 | Krajicek | |
| 5,527,322 A | 6/1996 | Klein et al. | |
| 5,536,251 A | 7/1996 | Evard et al. | |
| 5,540,716 A | 7/1996 | Hlavacek | |
| 5,544,802 A | 8/1996 | Crainich | |
| 5,560,532 A | 10/1996 | DeFonzo et al. | |
| 5,591,205 A | 1/1997 | Fowler | |
| 5,601,602 A | 2/1997 | Fowler | |
| 5,620,461 A | 4/1997 | Muijs et al. | |
| 5,634,936 A | 6/1997 | Lindon et al. | |
| 5,643,318 A | 7/1997 | Tsukernik et al. | |
| 5,645,565 A | 7/1997 | Rudd et al. | |
| 5,645,566 A | 7/1997 | Brenneman et al. | |
| 5,645,567 A | 7/1997 | Crainich | |
| 5,674,231 A | 10/1997 | Green et al. | |
| 5,676,689 A | 10/1997 | Kensey et al. | |
| 5,676,974 A | 10/1997 | Valdes et al. | |
| 5,683,405 A | 11/1997 | Yacoubian et al. | |
| 5,690,674 A | 11/1997 | Diaz | |
| 5,695,504 A | 12/1997 | Gifford, III et al. | |
| 5,695,505 A | 12/1997 | Yoon | |
| 5,716,375 A | 2/1998 | Fowler | |
| 5,725,554 A | 3/1998 | Simon et al. | |
| 5,728,114 A | 3/1998 | Evans et al. | |
| 5,728,122 A | 3/1998 | Leschinsky et al. | |
| 5,728,132 A | 3/1998 | Van Tassel et al. | |
| 5,728,133 A | 3/1998 | Kontos | |
| 5,762,872 A | 6/1998 | Buhler et al. | |
| 5,782,844 A | 7/1998 | Yoon et al. | |
| 5,782,860 A | 7/1998 | Epstein et al. | |
| 5,782,861 A | 7/1998 | Cragg et al. | |
| 5,797,960 A | 8/1998 | Stevens et al. | |
| 5,810,846 A | 9/1998 | Virnich et al. | |
| 5,810,851 A | 9/1998 | Yoon | |
| 5,817,113 A | 10/1998 | Gifford, III et al. | |
| 5,820,631 A | 10/1998 | Nobles | |
| 5,830,125 A | 11/1998 | Scribner et al. | |
| 5,853,421 A | 12/1998 | Leschinsky et al. | |
| 5,855,312 A | 1/1999 | Toledano | |
| 5,861,005 A | 1/1999 | Kontos | |
| 5,861,043 A | 1/1999 | Carn | |
| 5,871,474 A | 2/1999 | Hermann et al. | |
| 5,871,501 A | 2/1999 | Leschinsky et al. | |
| 5,871,525 A | 2/1999 | Edwards et al. | |
| 5,879,366 A | 3/1999 | Shaw et al. | |
| 5,902,310 A | 5/1999 | Foerster et al. | |
| 5,910,155 A | 6/1999 | Ratcliff et al. | |
| 5,919,207 A | 7/1999 | Taheri | |
| 5,922,009 A | 7/1999 | Epstein et al. | |
| 5,935,147 A | 8/1999 | Kensey et al. | |
| 5,941,890 A | 8/1999 | Voegele et al. | |
| 5,951,518 A | 9/1999 | Licata et al. | |
| 5,951,589 A | 9/1999 | Epstein et al. | |
| 5,957,940 A | 9/1999 | Tanner et al. | |
| 5,964,782 A | 10/1999 | Lafontaine et al. | |
| 5,972,034 A | 10/1999 | Hofmann et al. | |
| 5,984,934 A | 11/1999 | Ashby et al. | |
| 5,984,949 A | 11/1999 | Levin | |
| 6,004,341 A | 12/1999 | Zhu et al. | |

(56) References Cited

U.S. PATENT DOCUMENTS

| | | | |
|---|---|---|---|
| 6,007,563 A | 12/1999 | Nash et al. | |
| 6,022,372 A | 2/2000 | Kontos | |
| 6,024,756 A | 2/2000 | Huebsch et al. | |
| 6,036,720 A | 3/2000 | Abrams et al. | |
| 6,045,570 A | 4/2000 | Epstein et al. | |
| 6,048,358 A | 4/2000 | Barak | |
| 6,056,768 A | 5/2000 | Cates et al. | |
| 6,056,769 A | 5/2000 | Epstein et al. | |
| 6,056,770 A | 5/2000 | Epstein et al. | |
| 6,059,800 A | 5/2000 | Hart et al. | |
| 6,063,085 A | 5/2000 | Tay et al. | |
| 6,077,281 A | 6/2000 | Das | |
| 6,077,291 A | 6/2000 | Das | |
| 6,080,182 A | 6/2000 | Shaw et al. | |
| 6,080,183 A | 6/2000 | Tsugita et al. | |
| 6,090,130 A | 7/2000 | Nash et al. | |
| 6,110,184 A | 8/2000 | Weadock | |
| 6,113,612 A | 9/2000 | Swanson et al. | |
| 6,117,148 A | 9/2000 | Ravo | |
| 6,117,159 A | 9/2000 | Huebsch et al. | |
| 6,120,524 A | 9/2000 | Taheri | |
| 6,146,385 A | 11/2000 | Torrie et al. | |
| 6,149,660 A | 11/2000 | Laufer et al. | |
| 6,149,667 A | 11/2000 | Hovland et al. | |
| 6,152,937 A | 11/2000 | Peterson et al. | |
| 6,174,322 B1 | 1/2001 | Schneidt | |
| 6,197,042 B1 | 3/2001 | Ginn et al. | |
| 6,261,309 B1 * | 7/2001 | Urbanski | 606/213 |
| 6,273,903 B1 | 8/2001 | Wilk | |
| 6,277,140 B2 | 8/2001 | Ginn et al. | |
| 6,287,322 B1 | 9/2001 | Zhu et al. | |
| 6,302,898 B1 | 10/2001 | Edwards et al. | |
| 6,305,891 B1 | 10/2001 | Burlingame | |
| 6,309,416 B1 | 10/2001 | Swanson et al. | |
| 6,322,580 B1 | 11/2001 | Kanner | |
| 6,334,865 B1 | 1/2002 | Redmond et al. | |
| 6,348,064 B1 | 2/2002 | Kanner | |
| 6,355,052 B1 | 3/2002 | Neuss et al. | |
| 6,391,048 B1 | 5/2002 | Ginn et al. | |
| 6,398,752 B1 | 6/2002 | Sweezer et al. | |
| 6,402,765 B1 | 6/2002 | Monassevitch et al. | |
| 6,409,739 B1 * | 6/2002 | Nobles et al. | 606/148 |
| 6,419,669 B1 | 7/2002 | Frazier et al. | |
| 6,443,158 B1 | 9/2002 | Lafontaine et al. | |
| 6,450,391 B1 | 9/2002 | Kayan et al. | |
| 6,461,364 B1 | 10/2002 | Ginn et al. | |
| 6,488,692 B1 | 12/2002 | Spence et al. | |
| 6,494,848 B1 * | 12/2002 | Sommercorn et al. | 600/587 |
| 6,506,210 B1 | 1/2003 | Kanner | |
| 6,533,762 B2 | 3/2003 | Kanner et al. | |
| 6,547,806 B1 | 4/2003 | Ding | |
| 6,582,452 B2 | 6/2003 | Coleman et al. | |
| 6,602,263 B1 | 8/2003 | Swanson et al. | |
| 6,616,686 B2 | 9/2003 | Coleman et al. | |
| 6,623,510 B2 | 9/2003 | Carley et al. | |
| 6,626,918 B1 | 9/2003 | Ginn et al. | |
| 6,632,238 B2 | 10/2003 | Ginn et al. | |
| 6,634,537 B2 | 10/2003 | Chen | |
| 6,645,225 B1 * | 11/2003 | Atkinson | 606/213 |
| 6,652,538 B2 | 11/2003 | Kayan et al. | |
| 6,679,904 B2 | 1/2004 | Gleeson et al. | |
| 6,695,867 B2 | 2/2004 | Ginn et al. | |
| 6,719,777 B2 | 4/2004 | Ginn et al. | |
| 6,726,704 B1 | 4/2004 | Loshakove et al. | |
| 6,749,621 B2 | 6/2004 | Pantages et al. | |
| 6,749,622 B2 | 6/2004 | McGuckin et al. | |
| 6,755,842 B2 | 6/2004 | Kanner et al. | |
| 6,767,356 B2 | 7/2004 | Kanner et al. | |
| 6,780,197 B2 | 8/2004 | Roe et al. | |
| 6,790,220 B2 * | 9/2004 | Morris et al. | 606/213 |
| 6,846,319 B2 | 1/2005 | Ginn et al. | |
| 6,890,343 B2 * | 5/2005 | Ginn et al. | 606/213 |
| 6,896,692 B2 * | 5/2005 | Ginn et al. | 606/213 |
| 6,926,731 B2 | 8/2005 | Coleman et al. | |
| 6,942,674 B2 | 9/2005 | Belef et al. | |
| 7,001,398 B2 | 2/2006 | Carley et al. | |
| 7,025,776 B1 * | 4/2006 | Houser et al. | 606/213 |
| 7,108,709 B2 | 9/2006 | Cummins | |
| 7,111,768 B2 | 9/2006 | Cummins et al. | |
| 7,163,551 B2 | 1/2007 | Anthony et al. | |
| 7,211,101 B2 | 5/2007 | Carley et | |
| 7,431,729 B2 | 10/2008 | Chanduszko | |
| 7,582,104 B2 | 9/2009 | Corcoran et al. | |
| 7,806,904 B2 | 10/2010 | Carley et al. | |
| 7,819,895 B2 | 10/2010 | Ginn et al. | |
| 7,842,068 B2 | 11/2010 | Ginn | |
| 7,850,710 B2 * | 12/2010 | Huss | 606/213 |
| 7,854,810 B2 | 12/2010 | Carley et al. | |
| 7,857,828 B2 | 12/2010 | Jabba et al. | |
| 7,867,249 B2 | 1/2011 | Palermo et al. | |
| 7,879,071 B2 | 2/2011 | Carley et al. | |
| 7,887,555 B2 | 2/2011 | Carley et al. | |
| 7,887,563 B2 | 2/2011 | Cummins et al. | |
| 7,901,428 B2 | 3/2011 | Ginn et al. | |
| 7,905,900 B2 | 3/2011 | Palermo | |
| 7,918,873 B2 | 4/2011 | Cummins et al. | |
| 7,931,669 B2 | 4/2011 | Ginn et al. | |
| 8,083,768 B2 * | 12/2011 | Ginn et al. | 606/232 |
| 8,303,624 B2 * | 11/2012 | Fortson | 606/213 |
| 2001/0007077 A1 | 7/2001 | Ginn et al. | |
| 2001/0047180 A1 | 11/2001 | Grudem et al. | |
| 2002/0026215 A1 | 2/2002 | Redmond et al. | |
| 2002/0049427 A1 | 4/2002 | Wiener et al. | |
| 2002/0077656 A1 * | 6/2002 | Ginn et al. | 606/213 |
| 2002/0077657 A1 * | 6/2002 | Ginn et al. | 606/213 |
| 2002/0077658 A1 * | 6/2002 | Ginn | 606/213 |
| 2002/0082641 A1 | 6/2002 | Ginn et al. | |
| 2002/0107542 A1 | 8/2002 | Kanner et al. | |
| 2002/0151921 A1 | 10/2002 | Kanner et al. | |
| 2003/0004543 A1 | 1/2003 | Gleeson et al. | |
| 2003/0009180 A1 | 1/2003 | Hinchliffe et al. | |
| 2003/0093096 A1 | 5/2003 | McGuckin et al. | |
| 2003/0097140 A1 | 5/2003 | Kanner | |
| 2003/0109890 A1 | 6/2003 | Kanner et al. | |
| 2003/0125766 A1 | 7/2003 | Ding | |
| 2003/0158577 A1 | 8/2003 | Pantages et al. | |
| 2003/0158578 A1 | 8/2003 | Pantages et al. | |
| 2004/0073236 A1 | 4/2004 | Carley et al. | |
| 2004/0073255 A1 | 4/2004 | Ginn et al. | |
| 2004/0078053 A1 | 4/2004 | Berg et al. | |
| 2004/0087985 A1 | 5/2004 | Loshakove et al. | |
| 2004/0092973 A1 | 5/2004 | Chandusko et al. | |
| 2004/0127940 A1 * | 7/2004 | Ginn et al. | 606/213 |
| 2004/0143291 A1 | 7/2004 | Corcoran et al. | |
| 2004/0167570 A1 | 8/2004 | Pantages | |
| 2004/0254591 A1 | 12/2004 | Kanner et al. | |
| 2004/0267312 A1 | 12/2004 | Kanner et al. | |
| 2005/0090859 A1 | 4/2005 | Ravlkumar | |
| 2005/0119695 A1 | 6/2005 | Carley et al. | |
| 2005/0216057 A1 | 9/2005 | Coleman et al. | |
| 2005/0228443 A1 | 10/2005 | Yassinzadeh | |
| 2005/0267528 A1 * | 12/2005 | Ginn et al. | 606/214 |
| 2005/0273136 A1 | 12/2005 | Belef et al. | |
| 2005/0273137 A1 * | 12/2005 | Ginn | 606/213 |
| 2005/0274768 A1 | 12/2005 | Cummins et al. | |
| 2006/0167484 A1 | 7/2006 | Carley et al. | |
| 2006/0190014 A1 | 8/2006 | Ginn et al. | |
| 2006/0190036 A1 | 8/2006 | Wendel et al. | |
| 2006/0190037 A1 | 8/2006 | Ginn et al. | |
| 2006/0190038 A1 | 8/2006 | Carley et al. | |
| 2006/0195123 A1 | 8/2006 | Ginn et al. | |
| 2006/0195124 A1 | 8/2006 | Ginn et al. | |
| 2006/0287674 A1 | 12/2006 | Ginn et al. | |
| 2007/0027525 A1 | 2/2007 | Ben-Muvhar | |
| 2007/0083231 A1 | 4/2007 | Lee | |
| 2007/0270904 A1 * | 11/2007 | Ginn | 606/213 |
| 2007/0276416 A1 | 11/2007 | Ginn et al. | |
| 2007/0282352 A1 | 12/2007 | Carley et al. | |
| 2010/0114156 A1 * | 5/2010 | Mehl | 606/213 |
| 2010/0217132 A1 * | 8/2010 | Ellingwood et al. | 600/481 |
| 2011/0071565 A1 | 3/2011 | Ginn | |
| 2011/0106148 A1 | 5/2011 | Ginn et al. | |
| 2012/0035630 A1 | 2/2012 | Roorda | |
| 2012/0245603 A1 | 9/2012 | Voss | |

(56) References Cited

U.S. PATENT DOCUMENTS

| | | | |
|---|---|---|---|
| 2012/0245626 | A1 | 9/2012 | Ellingwood et al. |
| 2012/0296372 | A1* | 11/2012 | Ziobro .......................... 606/213 |
| 2012/0310261 | A1 | 12/2012 | Cummins et al. |
| 2013/0006274 | A1 | 1/2013 | Walberg et al. |

FOREIGN PATENT DOCUMENTS

| | | |
|---|---|---|
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| FR | 2 443 238 | 7/1980 |
| FR | 2 722 975 | 2/1996 |
| GB | 1 358 466 | 7/1974 |
| GB | 2 075 144 | 11/1981 |
| WO | WO 96/24291 | 8/1996 |
| WO | WO 97/07741 | 3/1997 |
| WO | WO 97/20505 | 6/1997 |
| WO | WO 98/17179 | 4/1998 |
| WO | WO 98/24374 | 6/1998 |
| WO | WO 98/25508 | 6/1998 |
| WO | WO 99/62408 | 12/1999 |
| WO | WO 00/06029 | 2/2000 |
| WO | WO 00/07505 | 2/2000 |
| WO | WO 00/07640 | 2/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/35832 | 5/2001 |
| WO | WO 01/49186 | 7/2001 |
| WO | WO 01/91628 | 12/2001 |
| WO | WO 02/19924 | 3/2002 |
| WO | WO 02/45593 | 6/2002 |
| WO | WO 02/45594 | 6/2002 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 2004/060169 | 7/2004 |
| WO | WO 2004/069054 | 8/2004 |
| WO | WO 2005/082256 | 9/2005 |
| WO | WO 2006/083889 | 8/2006 |
| ZA | 200100527 | 1/2001 |

OTHER PUBLICATIONS

U.S. Appl. No. 12/393,877, mailed Dec. 13, 2011, Office Action.
U.S. Appl. No. 12/684,562, mailed Dec. 28, 2011, Office Action.
U.S. Appl. No. 12/897,358, mailed Jan. 12, 2012, Notice of Allowance.
U.S. Appl. No. 12/941,809, mailed Dec. 13, 2011, Office Action.
U.S. Appl. No. 12/955,859, mailed Dec. 15, 2011 Office Action.
U.S. Appl. No. 12/941,809, mailed Jan. 30, 2012, Office Action.
U.S. Appl. No. 12/724,304, mailed Mar. 13, 2013, Issue Summary.
U.S. Appl. No. 13/308,227, mailed Nov. 30, 2011, Yibarren.
U.S. Appl. No. 13/525,718, filed Jun. 18, 2012, Carley et al.
U.S. Appl. No. 12/941/809, mailed Jun. 1, 2012, Office Action.
U.S. Appl. No. 09/866,551, filed May 25, 2001, Ginn.
U.S. Appl. No. 12/113,092, filed Apr. 30, 2008, Ginn et al.
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
U.S. Appl. No. 09/732,835, mailed Sep. 11, 2003, Office Action.
U.S. Appl. No. 09/732,835, mailed Feb. 9, 2004, Office Action.
U.S. Appl. No. 09/732,835, mailed Mar. 17, 2004, Notice of Allowance.
U.S. Appl. No. 10/006,400, mailed Aug. 27, 2004, Office Action.
U.S. Appl. No. 10/006,400, mailed Feb. 23, 2005, Office Action.
U.S. Appl. No. 10/006,400, mailed Apr. 11, 2005, Office Action.
U.S. Appl. No. 10/006,400, mailed Jul. 27, 2005, Office Action.
U.S. Appl. No. 10/006,400, mailed Mar. 6, 2006, Office Action.
U.S. Appl. No. 10/006,400, mailed May 24, 2006, Office Action.
U.S. Appl. No. 10/006,400, mailed Oct. 26, 2006, Office Action.
U.S. Appl. No. 10/006,400, mailed Apr. 19, 2007, Office Action.
U.S. Appl. No. 10/006,400, mailed Apr. 2, 2008, Office Action.
U.S. Appl. No. 10/006,400, mailed Jan. 2, 2009, Office Action.
U.S. Appl. No. 10/006,400, mailed Jul. 9, 2009, Notice of Allowance.
U.S. Appl. No. 10/006,400, mailed Jan. 13, 2010, Notice of Allowance.
U.S. Appl. No. 10/006,400, mailed Apr. 27, 2010, Notice of Allowance.
U.S. Appl. No. 10/006,400, mailed Aug. 2, 2010, Notice of Allowance.
U.S. Appl. No. 10/081,723, mailed Sep. 29, 2004, Office Action.
U.S. Appl. No. 10/081,723, mailed May 13, 2005, Notice of Allowance.
U.S. Appl. No. 11/198,811, mailed Aug. 26, 2008, Office Action.
U.S. Appl. No. 11/198,811, mailed Apr. 6, 2009, Office Action.
U.S. Appl. No. 11/198,811, mailed Sep. 22, 2009, Office Action.
U.S. Appl. No. 11/198,811, mailed Jun. 29, 2010, Notice of Allowance.
U.S. Appl. No. 11/198,811, mailed Oct. 20, 2010, Issue Notification.
U.S. Appl. No. 11/396,731, mailed Feb. 13, 2009, Office Action.
U.S. Appl. No. 11/396,731, mailed May 22, 2009, Office Action.
U.S. Appl. No. 11/396,731, mailed Jun. 29, 2010, Office Action.
U.S. Appl. No. 11/396,731, mailed Mar. 22, 2011, Office Action.
U.S. Appl. No. 11/744,089, mailed Nov. 26, 2008, Office Action.
U.S. Appl. No. 11/744,089, mailed Aug. 14, 2009, Office Action.
U.S. Appl. No. 12/955,859, mailed May 26, 2011, Office Action.
U.S. Appl. No. 12/955,859, mailed Jul. 21, 2011, Office Action.
U.S. Appl. No. 11/675,462, mailed Aug. 15, 2012, Issue Notification.
U.S. Appl. No. 11/744,089, mailed Aug. 8, 2012, Office Action.
U.S. Appl. No. 12/481,377, mailed Aug. 10, 2012, Notice of Allowance.
U.S. Appl. No. 12/724,304, mailed Jul. 11, 2012, Notice of Allowance.
U.S. Appl. No. 12/955,859, mailed Aug. 6, 2012, Office Action.
U.S. Appl. No. 11/396,731, mailed Sep. 1, 2011, Office Action.
U.S. Appl. No. 12/724,304, mailed Oct. 17, 2012, Issue Notification.
U.S. Appl. No. 11/744,089, mailed Apr. 15, 2013, Office Action.
U.S. Appl. No. 13/615,547, mailed Apr. 12, 2013, Notice of Allowance.
U.S. Appl. No. 12/955,859, mailed May 16, 2013, Office Action.
U.S. Appl. No. 11/344,891, mailed Jan. 22, 2013, Notice of Allowance.
U.S. Appl. No. 12/402,398, mailed Mar. 13, 2013, Notice of Allowance.
U.S. Appl. No. 12/608,769, mailed Feb. 27, 2013, Issue Notification.
U.S. Appl. No. 12/608,773, mailed Jan. 7, 2013, Office Action.
U.S. Appl. No. 12/961,331, mailed Feb. 1, 2013, Office Action.
U.S. Appl. No. 13/039,087, mailed Feb. 27, 2013, Issue Notification.
U.S. Appl. No. 13/153,594, mailed Jan. 29, 2013, Office Action.
U.S. Appl. No. 13/488,233, mailed Feb. 5, 2013, Notice of Allowance.
U.S. Appl. No. 13/490,143, mailed Jan. 4, 2013, Office Action.
U.S. Appl. No. 13/615,547, mailed Jan. 18, 2013, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 13/308,227, mailed Apr. 10, 2013, Office Action.
U.S. Appl. No. 11/744,089, mailed Aug. 8, 2013, Notice of Allowance.
U.S. Appl. No. 12/955,859, mailed Aug. 1, 2013, Notice of Allowance.

* cited by examiner

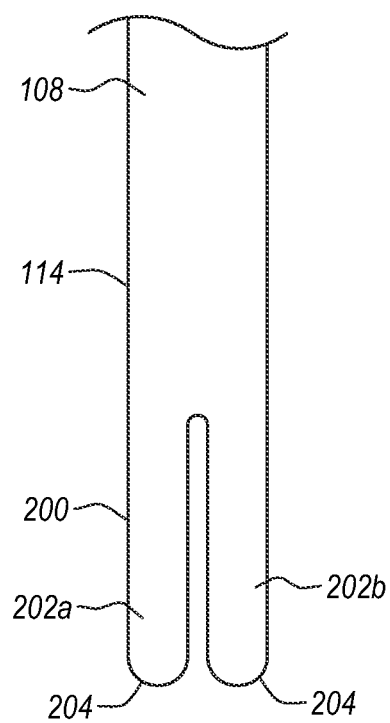
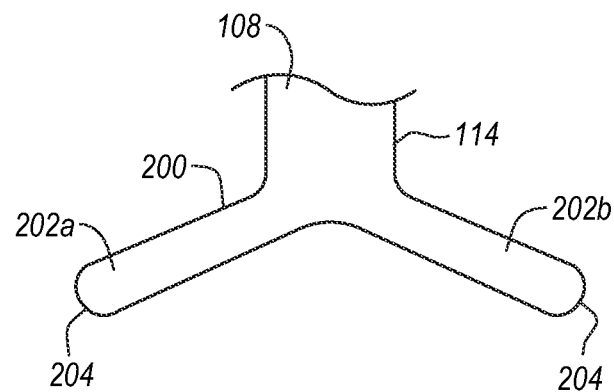
Fig. 2A
Fig. 2B
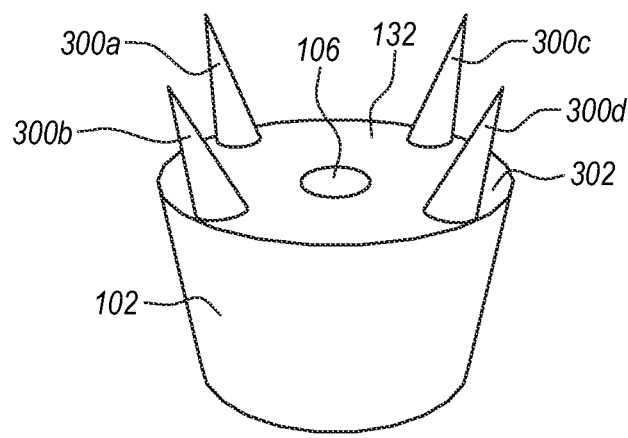
Fig. 3

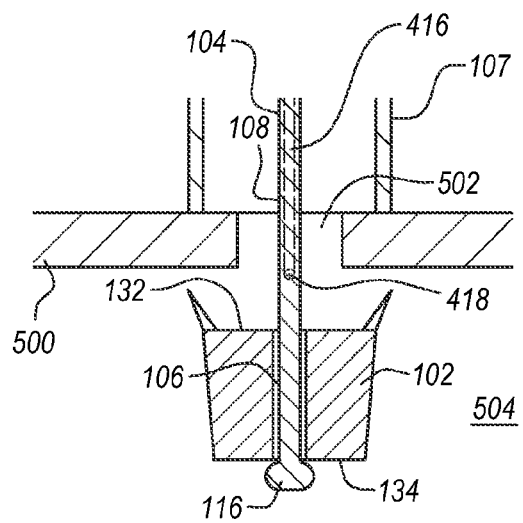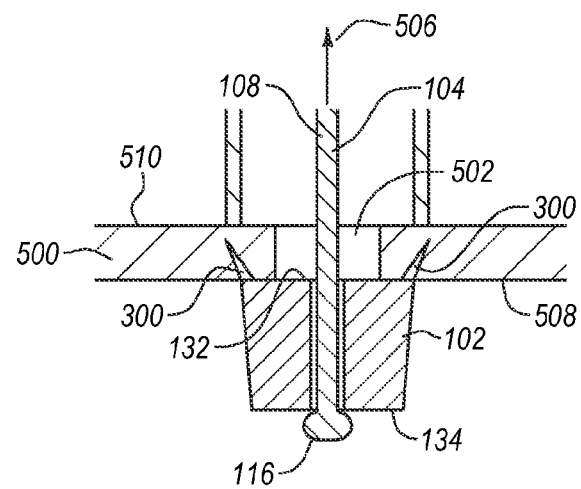
*Fig. 5A*  *Fig. 5B*
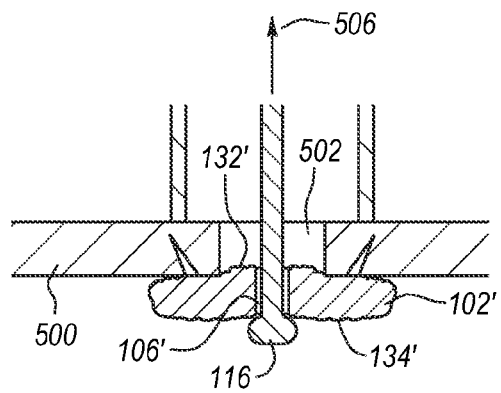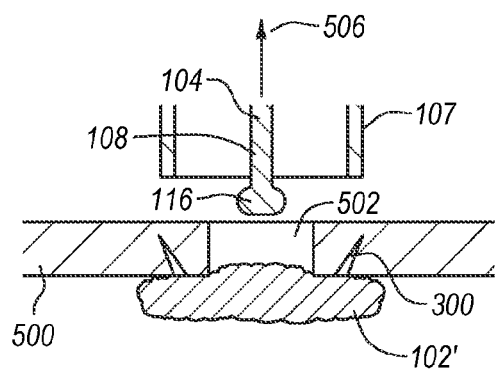
*Fig. 5C*  *Fig. 5D*

COLLAPSIBLE PLUG FOR TISSUE CLOSURE

CROSS-REFERENCE TO RELATED APPLICATIONS

Not Applicable.

BACKGROUND OF THE INVENTION

1. The Field of the Invention

The present disclosure generally relates to tissue closure apparatuses and methods.

2. The Relevant Technology

During intravascular and other related medical procedures, catheters are typically inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, stent delivery, plaque removal, and infusion of a therapeutic substance.

Often these procedures are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. The catheter typically is passed through the lumen of the introducer sheath and advanced over the guide wire into position for the medical procedure.

After the procedure is completed and the catheter and introducer sheath are removed from the patient, however, the access hole must be closed to prevent massive hemorrhage. This is typically achieved by applying pressure over the blood vessel manually and then by applying a pressure bandage or a compressive weight. With conventional methods, the rate of post-puncture hemorrhage is high, which can cause considerable complications. This impediment is exacerbated by the concomitant use of anticoagulant medications such as heparin or warfarin and by anti-platelet drugs, which are commonly used following a procedure in order to prevent clot formation and thrombus and/or to treat vascular disease.

It is generally recognized that many currently employed vascular sealing methods and devices and other tissue closure methods and devices incompletely seal holes or wounds in vascular or other tissue. Achieving complete wound closure is particularly important in sealing arterial punctures, which are relatively high pressure systems. For example, under normal blood pressure, the arterial system has a pressure of about 120/80 mmHg or more. Failure to completely close arterial holes can result in hematoma, exsanguination, and other catastrophic consequences, including limb amputation and death.

BRIEF SUMMARY OF THE INVENTION

The present disclosure provides methods and apparatuses that are suitable for closure of vascular punctures or other openings in bodily tissues.

One embodiment of a tissue closure device includes a collapsible plug and an actuator. The plug has a surface extending between a proximal face and an opposing distal face. A lumen extends through the plug between the proximal and distal faces along a longitudinal axis. The plug is collapsible between a non-collapsed state in which the lumen is open and a collapsed state in which the lumen is closed, and the plug is configured to close the opening in the tissue in the collapsed state. The actuator is configured to move the plug between the non-collapsed state and the collapsed state by being pulled through the lumen.

A plurality of tissue engaging members configured to engage an interior surface of the tissue can project from the proximal face of the plug. The actuator can include a shaft extending between a proximal end and a distal end, the shaft being sized to slide longitudinally through the lumen when the plug is in the non-collapsed state; and an engaging element positioned at the distal end of the shaft, the engaging element being configured to engage the distal face of the plug when the shaft is disposed within the lumen. The engaging element can have a larger cross-sectional size than the lumen and can be in the form of a knob or a plurality of retractable arms. A deployment apparatus can also be included to help deploy the plug.

Another embodiment of a tissue closure device includes a collapsible plug and an actuator. The plug has a surface extending between a proximal face and an opposing distal face. A lumen extends through the plug between the proximal and distal faces along a longitudinal axis. A plurality of tissue engaging members project from the proximal face and are configured to engage an inner surface of the tissue. The plug is configured to close the opening in the tissue when the plug is collapsed. The actuator has a shaft extending between a proximal end and a distal end with an engaging element positioned at the distal end. The shaft slidably engages with and extends through the lumen of the plug, and the engaging element engages with the distal face of the plug.

A deployment apparatus can also be included. The deployment apparatus can include a lumen extending therethrough that can be aligned with the lumen of the plug. The shaft of the actuator can extend through the lumen of the deployment apparatus. The plug can also be positioned within the lumen of the deployment apparatus.

One embodiment of a method of closing an opening in a body lumen includes the following: positioning a plug through the opening into the body lumen, the plug having a proximal face and an opposing distal face, an actuator being inserted into a lumen that extends between the proximal and distal faces of the plug; retracting the actuator to engage the distal face of the plug to the interior surface of the body lumen, to collapse the plug, and to close the lumen of the plug, thereby closing the opening; and removing the actuator from the body.

Additionally, the actuator can have an engaging element on an end thereof and can be inserted into the lumen of the plug such that the engaging element is positioned against the distal face of the plug and retracting the actuator can include retracting the actuator a first distance to collapse the plug upon itself. Retracting the actuator can further include retracting the actuator a second distance after the plug has collapsed to pass the engaging element through the lumen of the plug after which the lumen of the plug closes. The method can further include coupling the plug and actuator with a deployment apparatus before positioning the plug through the opening into the body lumen; and removing the deployment apparatus from the body in conjunction with removing the actuator from the body.

These and other embodiments and features of the present invention will become more fully apparent from the following description and appended claims, or may be learned by the practice of the invention as set forth hereinafter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements.

FIGS. 2A and 2B are side views of an alternative embodiment of an engaging element that can be used with the actuator of the closure device;

FIG. 3 is a perspective view of the plug of the closure device shown in FIG. 1;

FIGS. 5A-5D are cross sectional views of a closure device and a tissue wall, showing a method of closing an opening in the tissue wall.

DETAILED DESCRIPTION

As used in the specification and appended claims, directional terms, such as "top," "bottom," "up," "down," "upper," "lower," "proximal," "distal," and the like are used herein solely to indicate relative directions in viewing the drawings and are not intended to limit the scope of the claims in any way.

The present disclosure provides methods and apparatuses that are suitable for closure of vascular punctures or other openings in bodily tissues. The description included herein refers to "vessels" for convenience; the present disclosure is also applicable to facilitate closure of various types of other tissue openings, including by way of example only, surgical entry wound openings, and organ intrusion openings.

Figure 1:
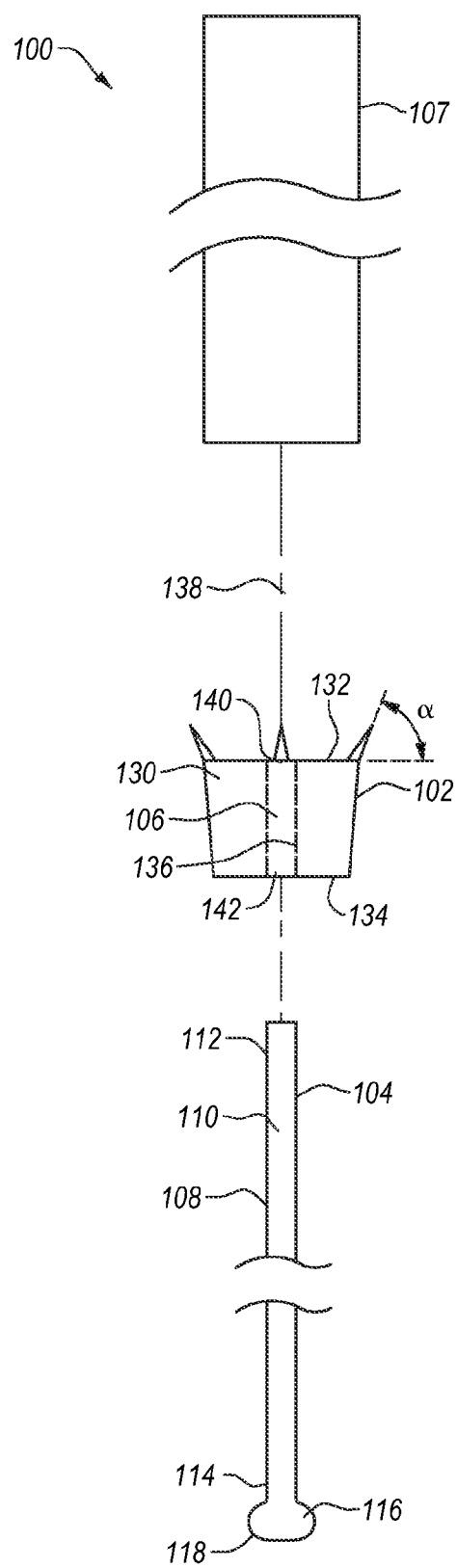
FIG. 1 is an exploded view of a closure device according to one embodiment of the present invention.

Referring now to FIG. 1, a closure device 100 for closing an opening in a tissue according to one embodiment of the present disclosure is depicted. Closure device 100 includes a collapsible plug 102 and an actuator 104 configured to collapse plug 102 by being pulled through a lumen 106 thereof, which becomes sealed after actuator 104 has been pulled therethrough. A deployment apparatus 107 can also be used, if desired, to initially position plug 102 and actuator 104 within the body.

As shown in FIG. 1, actuator 104 includes a generally cylindrical shaft 108 having an external surface 110 extending between a proximal end 112 and a spaced apart distal end 114. Shaft 108 has a diameter that is less than the diameter of lumen 106 formed in plug 102 so that shaft 108 can be slidably received within lumen 106. Shaft 108 can be fabricated from a metal, plastic, or other material having sufficient strength to apply and withstand a retracting force to plug 102, as discussed below. Alternatively, shaft 108 can be replaced by a wire, cord, cable, or the like, whether or not such shaft replacement is braided, non-braided, woven, or solid.

An engaging element 116 extends from distal end 114 of shaft 108. Engaging element 116 has a cross sectional size that is larger than the cross sectional size of lumen 106 formed in plug 102. In the depicted embodiment, engaging element 116 includes a single knob member 118 attached to or integrally formed with shaft 108. Knob member 118 is generally spherical in shape, although other configurations are possible. For instance, knob member 118 can be oblong, conical, or a variety of other shapes, as long as the cross sectional shape is such as will prevent knob member 118 from passing through lumen 106 of plug 102 until plug 102 has collapsed, as discussed below. Knob member 118 can be substantially rigid, pliable, flexible or resilient, or a combination thereof, and can be fabricated from metal, plastic, or other materials capable of providing the desired characteristics and properties of selectively preventing passage of the shaft through lumen 106 of plug 102. As discussed below, engaging element 116 is designed to pass through lumen 106 when a predetermined amount of force is applied. As such, either knob member 118 or lumen 106 or both can be designed to expand or collapse as desired to accomplish this.

Alternatively, the engaging element can include a plurality of elements spread apart from each other. For example, FIGS. 2A-2B depict an alternative embodiment of an engaging element 200 comprising a plurality of arms 202 positioned at distal end 114 of shaft 108 in a bifurcated fashion. Each arm 202 extends from shaft 108 to a distal end 204. Arms 202 are designed to be movable with respect to one another between a closed position, shown in FIG. 2A and an open position, shown in FIG. 2B.

In the closed position, arms 202 are positioned parallel to each other so that distal ends 204 thereof abut or are in close proximity one to another. In this closed position, arms 202 collectively have a similar cross sectional size to that of shaft 108 so as to fit within lumen 106 of plug 102.

In the open position, arms 202 extend away from a longitudinal axis of the shaft in different directions so that distal ends 204 are spaced apart from each other. In this open position, arms 202 collectively have a larger cross sectional size than lumen 106 of plug 102 (FIG. 1) and are initially prevented from entering into lumen 106 of plug 102 (FIG. 1). Arms 202 are designed to bias toward the open position. That is, when the arms are freely exposed, they will remain in the open position until a predetermined force causes arms 202 to move from the open to the closed position. The arms 202 will then remain in the closed position until the force is removed. For example, the arms can be maintained in the closed position when positioned inside a restricting lumen or the like. Although only two arms 202 are shown in the depicted embodiment, any number of arms can be used. For example, three, four, or more arms can be used.

It is appreciated that the foregoing are only examples of engaging elements that can be used with the present invention and that other shapes, sizes, number of elements, etc. can alternatively be used, as long as the engaging element is prevented from passing through the lumen of the plug until the plug has collapsed, as discussed below.

Returning to FIG. 1, plug 102 includes a generally cylindrical or frustoconical body having an outer surface 130 extending between a proximal face 132 and an opposing distal face 134. Proximal and distal faces 132 and 134 are generally parallel to each other, although this is not required. Lumen 106 is bounded by an inside surface 136 that extends through plug 102 along a longitudinal axis 138 between a proximal opening 140 formed on proximal face 132 and a distal opening 142 formed on distal face 134. Proximal and distal openings 140 and 142 are generally centered on proximal and distal faces 132 and 134, although this is not required.

Lumen 106 has a cross sectional size that is larger than the cross sectional size of shaft 108, but smaller than the cross sectional size of engaging element 116. As such, when plug 102 is in the non-collapsed state, shaft 108 can be received and pass through lumen 106 whereas engaging element 116 cannot. If an engaging element having multiple members is used, such as engaging element 200 discussed above, that engaging element is prevented from passing through lumen 106 while the members (e.g., arms 202) are in the open position.

Plug 102 is designed to collapse when a predetermined amount of retracting force is applied between proximal and distal faces 132 and 134. When this occurs, proximal and distal faces 132 and 134 move toward each other. As discussed above, lumen 106 is sized such that the engaging element is prevented from passing therethrough in the non-collapsed state. As such, when the predetermined amount of force is applied to engaging element 116 through shaft 108, the force is directed to distal face 134 by the engaging element, which causes plug 102 to collapse.

Plug 102 is also designed so that engaging element 116 will pass through lumen 106 when a second predetermined amount of retracting force is applied that is greater than the first predetermined amount of retracting force. This can be accomplished by plug 102 being fabricated from a flexible material that allows lumen 106 to expand to a size that will allow engaging element 116 to pass therethrough. Alternatively, an engaging element 116 can be used that compresses or collapses to fit within lumen 106.

Alternatively, in some embodiments the engaging element can move to a closed state to pass through lumen 106. For example, engagement element 200, discussed above, can be designed such that when the second predetermined amount of refracting force is reached, the force between distal face 134 and arms 202 causes arms 202 to move to the closed position, (See FIG. 2A), thereby allowing arms 202 to retract into and pass through lumen 106. Stated another way, plug 102 will deform, i.e., collapse, prior to deformation of arms 202.

Thus, plug 102 is first collapsed after which engaging element 116 passes through lumen 106 as a retracting force is applied to actuator 104. Plug 102 may be formed from biocompatible materials, from bioabsorbable materials, or combinations of biocompatible and/or bioabsorbable materials, and/or may be substantially rigid, pliable, flexible, or resilient, or a combination thereof, depending on the makeup of knob member 118. Examples of materials that can be used for plug 102 include silicone, polyurethane, collagen, poly lactic acid (PLA), poly-l-lactic acid (PLLA), copoly lactic acid/glycolic acid (PLGA), Polyethylene glycol (PEG), Polyglycolic Acid (PGA), or any combination thereof. For example, collagen within a Polyglycolic Acid mesh may be used to form the plug structure.

As shown in FIG. 3, a plurality of tissue engaging members 300 can extend proximally away from proximal face 132 of plug 102. Tissue engaging members 300 are configured to engage the interior surface of the tissue about the opening when plug 102 is positioned thereat. Each tissue engaging member 300 extends from proximal face 132 at or near a circumferential edge 302 thereof and, as illustrated, are generally evenly spaced around the edge. Tissue engaging members 300 can extend in a substantially orthogonal direction from proximal face 132 (i.e., substantially parallel to longitudinal axis 138) or can extend radially out from proximal face 132 so as to extend over and past circumferential edge 302. As such, tissue engaging members 300 can form an angle α with respect to proximal face 132 (See FIG. 1) of between about 90 degrees to about 45 degrees. Other angles are also possible, including angles between 90 and 120 degrees.

In some embodiments, tissue engaging members 300 are resiliently movable radially inward to fit within deployment apparatus 107, as discussed in more detail below. For example, one or more tissue engaging members 300 may form an angle of about 45 degrees with respect to proximal face, as discussed above, yet be pivotable or otherwise movable to a substantially orthogonal direction to proximal face 132 to fit within deployment apparatus 107 during deployment (see, e.g., FIG. 4A). Then, when plug 102 has exited from deployment apparatus 107, tissue engaging members 300 can move back to their original position of about 45 degrees from proximal face 132.

Although four tissue engaging members 300 are shown in the depicted embodiment, any number of tissue engaging members can be used. Furthermore, tissue engaging members 300 or groups of tissue engaging members 300 can be evenly spaced from each other and/or unequally spaced. Tissue engaging members 300 can be substantially straight, or curved, or have an irregular shape. In addition, tissue engaging members 300 can have barbs, or other structures extending from a main body of a tissue engaging member, formed thereon to prevent tissue engaging members 300 from backing out of the tissue once engaged therewith. Tissue engaging members 300 can be fabricated from a rigid, biocompatible material, such as Nitinol (a nickel-titanium alloy), titanium, steel, polycarbonates, polypropylene, or other molded polymers. Additionally, the tissue engaging members may be fabricated from rigid bioabsorbable materials such as poly lactic acid (PLA), poly-l-lactic acid (PLLA), copoly lactic acid/glycolic acid (PLGA), Polyethylene glycol (PEG), or Polyglycolic Acid (PGA), or the like. Further, it will be appreciated by those skilled in the art, that the tissue engaging members on a single plug can be different or the same and/or groups of tissue engaging members on a single plug can be different or the same.

As noted above, lumen 106 is designed to become sealed after engaging element 116 has been pulled therethrough when plug 102 is in the collapsed state. This can be accomplished in various ways. For example, in one embodiment, a sealing member 440 (see FIG. 4C) may be provided within lumen 106 for substantially sealing lumen 106 from fluid flow therethrough. Sealing member 440 can be formed from a material that expands when exposed to fluids, e.g., a gel foam, and may be bioabsorbable, if desired. Sealing member 440 can be positioned about the inside surface of lumen 106 so that lumen 106 is open before exposure to fluid, thereby allowing actuator 104 to be positioned therein. Upon exposure to fluid, e.g., blood, sealing member 440 may expand, e.g., due to hydration and the like, across lumen 106 and/or otherwise substantially seal lumen 106. Thus, when engaging element 116 is pulled through lumen 106 and removed therefrom, the fluid can contact sealing member 440, expanding the sealing member to seal the lumen.

Alternatively, sealing member 440 may be a valve or coil of material that is biased to substantially seal lumen 106 from fluid flow. For example, the sealing member may be biased to substantially seal lumen 106, yet may be deflected to accommodate insertion of actuator 104 therethrough. In a further alternative, lumen 106 may have a relatively small cross-section, and sealing member 440 may be omitted. For example, this may be a good option if shaft 108 of actuator 104 is replaced with a wire, cable, or cord.

In one alternative embodiment, plug 102 can be fabricated from a material that pushes inward into lumen 106 when plug 102 collapses so as to close and seal lumen 106. Examples of this type of material include silicone, collagen, or a combination of collagen within bioabsorbable polymer mesh. In another alternative embodiment, plug 102 can be fabricated from a material that naturally biases inward, even in the non-collapsed state. In this embodiment, actuator 104 keeps lumen 106 open until actuator 104 is removed, whether plug 102 is in the collapsed state or not. Exemplary materials could include, for example, latex foam or polyurethane. In another alternative embodiment, plug 102 can be designed to twist when collapsing so as to seal lumen 106. Other alternatives may also be possible.

Figure 4A:
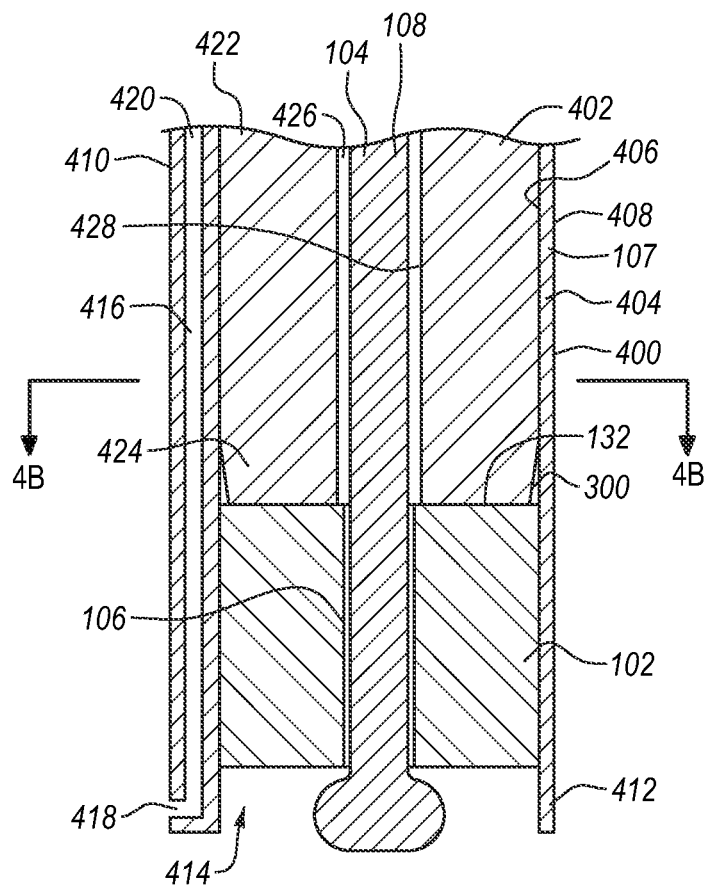
FIGS. 4A and 4B are cross sectional views of an assembled closure device in which the plug and actuator are positioned within a deployment apparatus.
Figure 4B:
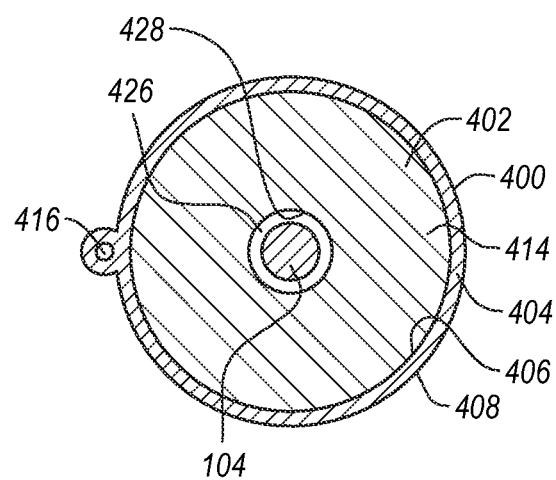
Figure 4C:
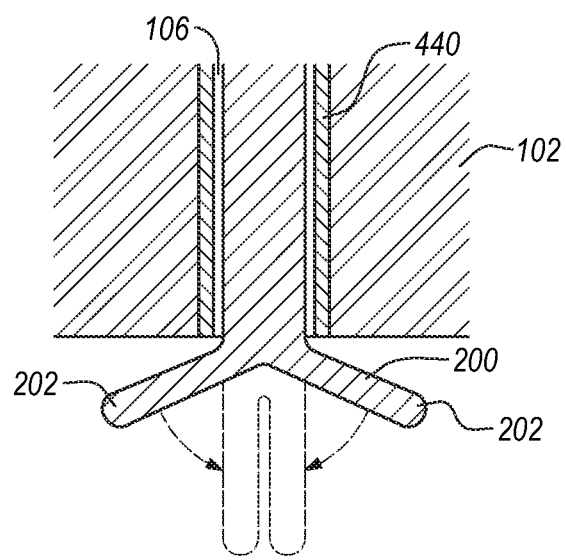
FIG. 4C is a cross sectional view of an assembled closure device in which the plug and actuator are positioned within a deployment apparatus and where the engaging element includes arms.

Turning to FIGS. 4A-4C, deployment apparatus 107 is fabricated from an introducer sheath 400 and a deployment member 402 positioned therein. Introducer sheath 400 is a generally cylindrical body having a perimeter side wall 404 having an inner surface 406 and an opposing outer surface 408 extending between a proximal end 410 and a distal end 412. Inner surface 406 bounds a lumen 414 that extends longitudinally through introducer sheath 400 and is configured to receive shaft 108 of actuator 104. In some embodiments, such as the embodiment depicted in FIG. 4A, introducer sheath 400 is also configured to receive plug 102 as well as engaging element 116 at distal end 412. It is appreciated that engaging element 200 can be replaced by engaging element 116, as shown in FIG. 4C, or by any other type of engaging element envisioned herein.

A bleed back lumen 416, as is known in the art, can also be formed in introducer sheath 400. Bleed back lumen 416 extends between an input port 418 formed on outer surface 408 at or near distal end 412 and an output port 420 disposed at or near proximal end 410. When bleed back lumen 416 enters the blood vessel, the pressure of the blood will cause blood to flow through bleed back lumen 416 from input port 418 to output port 420, thereby indicating that input port 418 has entered the blood vessel. When introducer sheath is in this position, plug will be positioned within the vessel when plug is subsequently ejected from introducer sheath 400.

Alternatively, when a deployment apparatus 107 is not used, bleed back lumen 416 can be incorporated within shaft 108 of actuator 104, e.g., as shown in dashed line in FIG. 5A. It is noted that when bleed back lumen 416 is incorporated within actuator 104, input port 418 can be positioned on shaft 108 so as to lie proximally of proximal face 132 of plug 102 when actuator 104 has been inserted therein. As a result, blood will only flow through bleed back lumen 416 when plug 102 is completely within the vessel. Alternatively, introducer sheath 400 or actuator 104 may include one or more depth markers (not shown) for the medical personnel to use in monitoring the insertion, or the closure device can include one or more radiopaque markers (not shown) and be positioned within the vessel using fluoroscopy or other imaging system to monitor the insertion.

Deployment member 402 extends from a proximal end 422 to a distal end 424 and is positioned within lumen 414 of introducer sheath 400 so that distal end 424 abuts proximal face 132 of plug 102 when plug 102 is positioned within introducer sheath 400, as shown in FIG. 4A. A lumen 426 bounded by an inside surface 428 extends through deployment member 402 between proximal and distal ends 422 and 424. Lumen 426 is positioned within deployment member 402 such that lumen 426 aligns with lumen 106 of plug 102 when plug 102 is positioned within introducer sheath 400. This allows shaft 108 of actuator 104 to also pass through lumen 426.

During use, once introducer sheath 400 has been positioned within the blood vessel as indicated by bleed back lumen 416 or the like as discussed above, the physician or other medical personnel can push deployment member 402 distally within introducer sheath 400. The ensuing pushing force of distal end 424 of deployment member 402 against proximal face 132 of plug 102 causes plug 102 to exit introducer sheath 400 out of distal end 412 thereof.

In some embodiments, introducer sheath 400 includes the same introducer sheath used for the underlying medical procedure. As noted above, an original introducer sheath and guidewire are often used during the underlying medical procedure through which a catheter or other device is passed. As such, once the catheter is removed from the original introducer sheath, the sheath and/or guidewire can be kept in place and plug 102 and actuator 104 can be inserted therethrough into the vessel, using the guidewire, if desired. Deployment member 402 can then be inserted through the original introducer sheath to push plug 102 out of the original introducer sheath and into the vessel.

Furthermore, even if the original introducer sheath is not used, the guidewire can be used to guide the closure device into the vessel. To facilitate this, a guide lumen (not shown) can extend through shaft 108 and engaging element 116 of the actuator. The plug/actuator combination is then guided to the opening by receiving the guidewire into the guide lumen and moving the combination down the guide wire into the vessel.

Turning to FIGS. 5A-D, a method of sealing and/or closing a passage through tissue, such as an opening 502 communicating with a blood vessel or other body lumen 504 through a wall 500 thereof will now be discussed. Applicant notes that the disclosed method is exemplary only and that other methods of sealing and/or closing a passage through tissue can also be performed.

Initially, shaft 108 of actuator 102 is positioned within lumen 106 of plug 102 with engaging element 116 abutting distal surface 134 of plug 102, as shown in FIG. 5A. Then, the plug/actuator combination is inserted into body lumen 504 through opening 502. This can be done with or without a deployment apparatus 107, as described above, using a bleed back lumen 416 or other indicating method or apparatus known in the art to indicate when plug 102 is in position. If a deployment apparatus 107 is used, deployment member 402 may be used to expel plug 102 out of introducer sheath 400 and into body lumen 504.

If the original introducer sheath used for the underlying medical procedure is employed, an indicating method or apparatus may not be required as the original introducer sheath may already extend into lumen 504 by virtue of the use of the original introducer sheath in the underlying medical procedure. When plug 102 is in position within body lumen 504, shaft 108 of actuator 102 extends through opening 502 and out of the body.

Once plug 102 is positioned within body lumen 504, deployment apparatus 107, if used, is then retracted through opening 502 so as to be positioned outside of body lumen 502, as shown in FIG. 5A.

An external retracting force, denoted by arrow 506 in FIG. 5B is then applied to actuator 104 by pulling proximally on shaft 108. Because engaging element 116 contacts distal face 134 of plug 102, retracting force 506 is thereby applied against plug 102. This causes plug 102 to be moved proximally toward opening 502 in vessel wall 500. As plug 102 moves toward vessel wall 500, tissue engaging members 300 engage an inner surface 508 of wall 500 and extend into the wall. Plug 102 continues moving distally until proximal face 132 contacts inner surface 508 of vessel wall 500 surrounding opening 502, as shown in FIG. 5B. Vessel wall 500 prevents plug 102 from retracting further. If a deployment apparatus 107 is used, it can be maintained against an outer surface 510 of vessel wall 500 opposing inner surface 508, as shown, to provide further support to vessel wall 500 to prevent plug 102 from retracting further. Tissue engaging members 300 can extend all the way through vessel wall 500 or only partially through.

The external retracting force 506 is maintained. At a first predetermined amount of retracting force imposed by engaging element 116 against distal face 134 of plug 102, plug 102 collapses, going from the non-collapsed state shown in FIG. 5B to the collapsed state shown in FIG. 5C. For clarity of discussion, the structural elements of plug 102 are labeled with an apostrophe in the collapsed state (e.g., plug 102', proximal face 132', etc.). Some of the plug material may extend into opening 502 when plug 102' is in the collapsed state. In the collapsed state proximal and distal faces 132' and 134' are closer to one another than in the non-collapsed state.

The external retracting force 506 is increased. At a second predetermined amount of retracting force that is greater than the first predetermined amount, engaging element 116 enters and passes proximally completely through lumen 106' of plug 102'. As shown in FIG. 5D, after engaging element 116 has passed therethrough, lumen 106' becomes closed or sealed by the force of collapsed plug 102', or by using a sealing member or by other means, as discussed above.

Once engaging element 116 has passed through lumen 106', actuator 104 is removed from the body, leaving collapsed plug 102' secured to inner surface 508 of vessel wall 500 by tissue engaging members 300. If a deployment apparatus 107 is used, it too is removed from the body.

Although the method described above in conjunction with FIGS. 5A-5D employs engaging element 116, it is appreciated that other engaging elements, as envisioned or described herein, can alternatively be used. For example, engaging element 200 can be used in place of engaging element 116, as shown in FIG. 4C. When engaging element 200 is used, arms 202 remain in the open position represented by the solid lines in FIG. 4C while plug 102 is positioned within body lumen 504. As a result, arms 202 cause retracting force 506 to be applied against plug 102 until plug 102 collapses by the first predetermined amount of retracting force, similar to that described above. The second predetermined amount of retracting force between arms 202 and collapsed plug 102' then causes arms 202 to move to the closed position represented by the dashed line in FIG. 4C, which allows engaging element 200 to then pass through lumen 106' and be removed, as discussed above.

Although the present invention has been described in considerable detail with reference to certain preferred embodiments, it is contemplated that one skilled in the art may make modifications to the device herein without departing from the scope of the invention. Therefore, the scope of the appended claims should not be considered limited to the embodiments described herein

What is claimed is:

1. A closure device for closing an opening in tissue having an interior surface, the closure device comprising:
    a collapsible plug having an outer surface extending between a proximal face and an opposing distal face, a lumen extending through the plug between the proximal and distal faces along a longitudinal axis, the plug being collapsible between a non-collapsed state in which the lumen is open and a collapsed state in which the lumen is closed, the plug being configured to close the opening in the tissue in the collapsed state; and
    an actuator configured to move the plug between the non-collapsed state and the collapsed state by being pulled through the lumen from a distal end of the lumen formed at the distal face of the plug to the proximal face of the plug.

2. The closure device recited in claim 1, wherein the distance between the proximal face and the distal face is less when the plug is in the collapsed state than when the plug is in the non-collapsed state.

3. The closure device recited in claim 1, wherein the plug further comprises a plurality of tissue engaging members projecting from the proximal face, the tissue engaging members being configured to engage the interior surface of the tissue.

4. The closure device recited in claim 3, wherein the tissue engaging members project from the proximal face at or near a circumferential edge thereof.

5. The closure device recited in claim 1, wherein the plug is generally frustoconically shaped in the non-compressed state.

6. The closure device recited in claim 1, wherein a predetermined retracting force imposed by the actuator on the distal face moves the plug from the non-collapsed state to the collapsed state.

7. The closure device recited in claim 1, wherein the actuator comprises:
    a shaft extending between a proximal end and a distal end, the shaft being sized to slide longitudinally through the lumen when the plug is in the non-collapsed state; and
    an engaging element positioned at the distal end of the shaft, the engaging element being configured to engage the distal face when the shaft is disposed within the lumen.

8. The closure device recited in claim 7, wherein the engaging element has a larger cross-sectional size than the lumen.

9. The closure device recited in claim 7, wherein the engaging element comprises a plurality of retractable arms.

10. The closure device recited in claim 7, wherein a first predetermined retracting force imposed by the engaging element against the distal face moves the plug from the non-collapsed state to the collapsed state.

11. The closure device recited in claim 10, wherein the plug is configured to allow the engaging element to pass through the lumen upon imposition of a second predetermined amount of retracting force that is greater than the first predetermined retracting force and to close the lumen after the engaging element has passed therethrough.

12. The closure device recited in claim 1, further comprising a deployment apparatus extending between a proximal end and a distal end, a lumen extending through the deployment apparatus, the deployment apparatus being configured to receive the actuator within the lumen.

13. The closure device recited in claim 12, wherein the deployment apparatus is configured to receive the plug within the lumen.

14. A closure device for closing an opening in tissue having an interior surface and an exterior surface, the closure device comprising:
    a collapsible plug having a surface extending between a proximal face configured to engage the interior surface of the tissue and an opposing distal face, a lumen extending through the plug between the proximal and distal faces along a longitudinal axis, a plurality of tissue engaging members projecting from the proximal face and configured to engage the interior surface of the tissue, the plug being collapsible between a non-collapsed state in which the lumen is open and a collapsed state in which the lumen is closed, the plug being configured to close the opening in the tissue when the plug is collapsed and a portion of the proximal face of the plug enters the opening in tissue; and
    an actuator having a shaft extending between a proximal end and a distal end, an engaging element being positioned at the distal end of the shaft, the shaft slidably engaging with and extending through the lumen of the plug, and the engaging element engaging with the distal face of the plug, the actuator being configured to move the plug between the non-collapsed state and the collapsed state by being pulled through the lumen from a distal end of the lumen formed at the distal face of the plug to the proximal face of the plug.

15. The closure device recited in claim 14, wherein the tissue engaging members project from the proximal face at or near a circumferential edge thereof.

16. The closure device recited in claim 14, wherein the engaging element has a larger cross-sectional size than the lumen.

17. The closure device recited in claim 14, further comprising a deployment apparatus extending between a proximal end and a distal end, a lumen extending through the deployment apparatus and being aligned with the lumen of the plug, the shaft of the actuator extending through the lumen of the deployment apparatus.

18. The closure device recited in claim 17, wherein the lumen of the deployment apparatus includes a portion at the distal end that is sized to receive the engaging element.

19. The closure device recited in claim 17, wherein the plug is positioned within the lumen of the deployment apparatus.

* * * * *